US012265068B2

(12) United States Patent
Jung et al.

(10) Patent No.: US 12,265,068 B2
(45) Date of Patent: Apr. 1, 2025

(54) GAS DETECTION APPARATUS AND GAS DETECTION METHOD FOR CELL MODULE ASSEMBLIES

(71) Applicant: LG ENERGY SOLUTION, LTD., Seoul (KR)

(72) Inventors: Young Sung Jung, Daejeon (KR); Sang Jin Lee, Daejeon (KR); Seung Hee Chae, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 273 days.

(21) Appl. No.: 17/913,988

(22) PCT Filed: Jul. 29, 2021

(86) PCT No.: PCT/KR2021/009937
§ 371 (c)(1),
(2) Date: Sep. 23, 2022

(87) PCT Pub. No.: WO2022/025688
PCT Pub. Date: Feb. 3, 2022

(65) Prior Publication Data
US 2023/0130328 A1    Apr. 27, 2023

(30) Foreign Application Priority Data
Jul. 29, 2020  (KR) ......................... 10-2020-0094310

(51) Int. Cl.
G01N 33/00    (2006.01)
G01M 3/16    (2006.01)
H01M 10/42    (2006.01)

(52) U.S. Cl.
CPC .......... *G01N 33/0031* (2013.01); *G01M 3/16* (2013.01); *H01M 10/4228* (2013.01)

(58) Field of Classification Search
CPC .......... H01M 10/4228; G01N 33/0031; G01N 33/0062
See application file for complete search history.

(56) References Cited

U.S. PATENT DOCUMENTS 9,470,602 B2 * 10/2016 Yasooka ............... G01M 3/363
11,569,553 B2 * 1/2023 Golubkov ............. B60L 3/0046
(Continued)

FOREIGN PATENT DOCUMENTS

| CN | 108444650 A | 8/2018 | |
| CN | 109596272 A * | 4/2019 | ............. G01M 3/04 |

(Continued)

OTHER PUBLICATIONS

International Search Report (PCT/ISA/210) issued in PCT/KR2021/009937 mailed on Nov. 8, 2021.
(Continued)

*Primary Examiner* — Justin N Olamit
(74) *Attorney, Agent, or Firm* — Birch, Stewart, Kolasch & Birch, LLP

(57) ABSTRACT

A gas detection apparatus for cell module assemblies accurately and rapidly detects a damaged cell of a cell module assembly and the damaged position of the damaged cell. The gas detection apparatus includes a gas detection chamber configured to receive a cell module assembly; and a sliding die configured to be movable to the lower part of the gas detection chamber in the state in which the cell module assembly is disposed at the upper end thereof. The gas detection apparatus further includes a gas sensor provided in the gas detection chamber, the gas sensor including a plurality of gas sensors disposed so as to correspond to positions of cells of the cell module assembly. A gas detection method for cell module assemblies uses the gas detection apparatus for cell module assemblies.

11 Claims, 11 Drawing Sheets

(56) References Cited

U.S. PATENT DOCUMENTS

| | | | |
|---|---|---|---|
| 2014/0174150 A1* | 6/2014 | Yajima | H01M 10/48 429/82 |
| 2015/0020578 A1* | 1/2015 | Kim | G01M 3/363 73/40 |
| 2016/0226093 A1 | 8/2016 | Edmonston et al. | |
| 2018/0067013 A1 | 3/2018 | Son | |
| 2019/0148760 A1 | 5/2019 | Edmonton et al. | |
| 2020/0256921 A1* | 8/2020 | Hwang | G01N 1/24 |
| 2021/0020997 A1 | 1/2021 | Lee et al. | |
| 2021/0305603 A1* | 9/2021 | Okabe | H01M 8/04679 |
| 2022/0209276 A1 | 6/2022 | Edmonston et al. | |

FOREIGN PATENT DOCUMENTS

| | | | |
|---|---|---|---|
| KR | 10-2009-0108478 A | 10/2009 | |
| KR | 10-2012-0115835 A | 10/2012 | |
| KR | 101198857 B1 * | 11/2012 | |
| KR | 10-2016-0052217 A | 5/2016 | |
| KR | 10-2016-0072571 A | 6/2016 | |
| KR | 10-2017-0041103 A | 4/2017 | |
| KR | 10-2018-0028266 A | 3/2018 | |
| KR | 10-2018-0047359 A | 5/2018 | |
| KR | 10-2019-0079798 A | 7/2019 | |
| KR | 10-2019-0139122 A | 12/2019 | |
| KR | 10-2020-0084530 A | 7/2020 | |
| WO | WO 2019/177288 A1 | 9/2019 | |
| WO | WO 2019/215339 A1 | 11/2019 | |

OTHER PUBLICATIONS

Extended European Search Report for European Application No. 21849781.6, dated Jul. 4, 2024.

* cited by examiner

[FIG. 1]
10
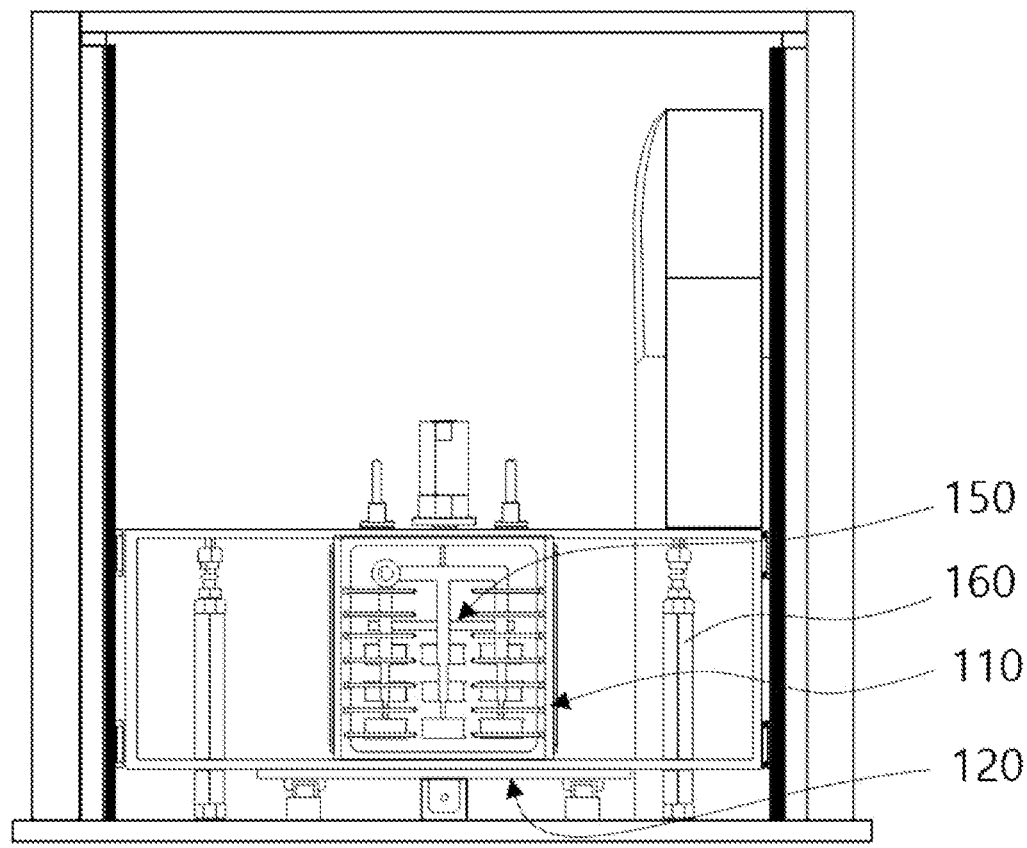

[FIG. 2]
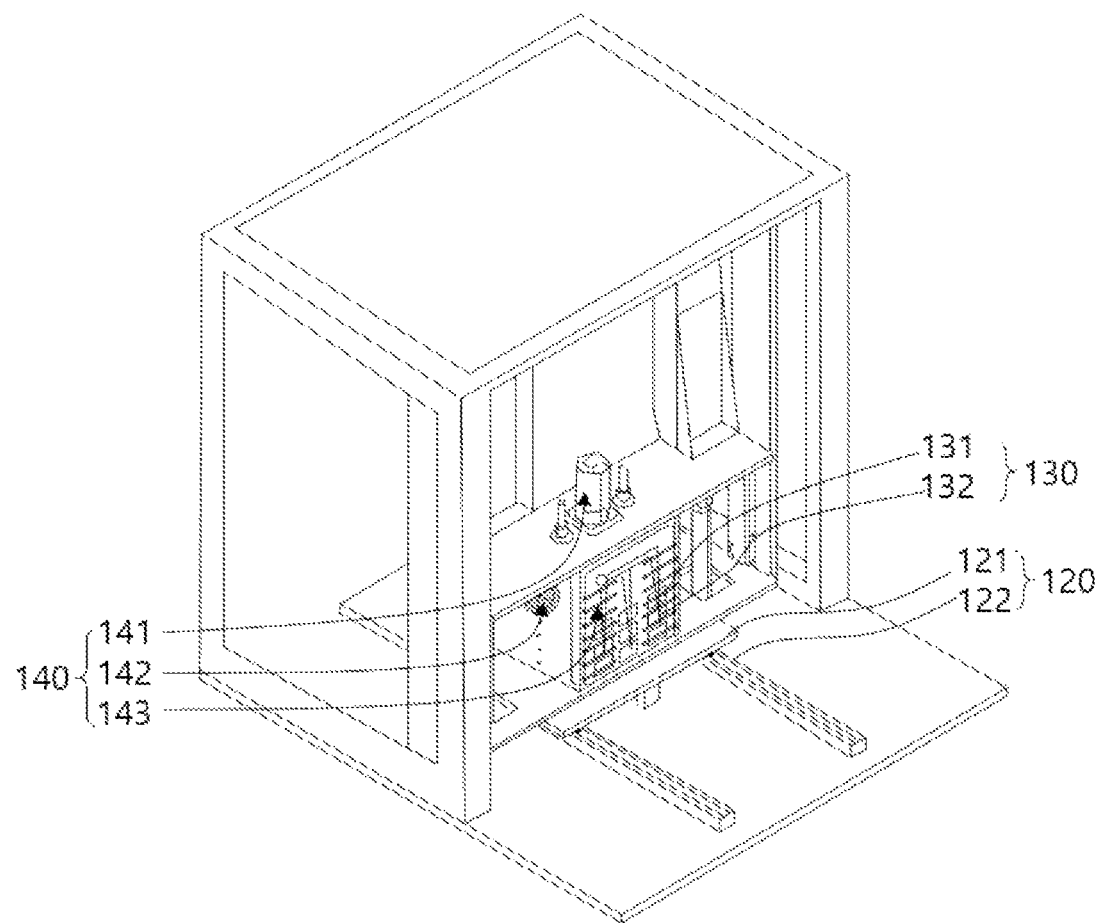

[FIG. 3]
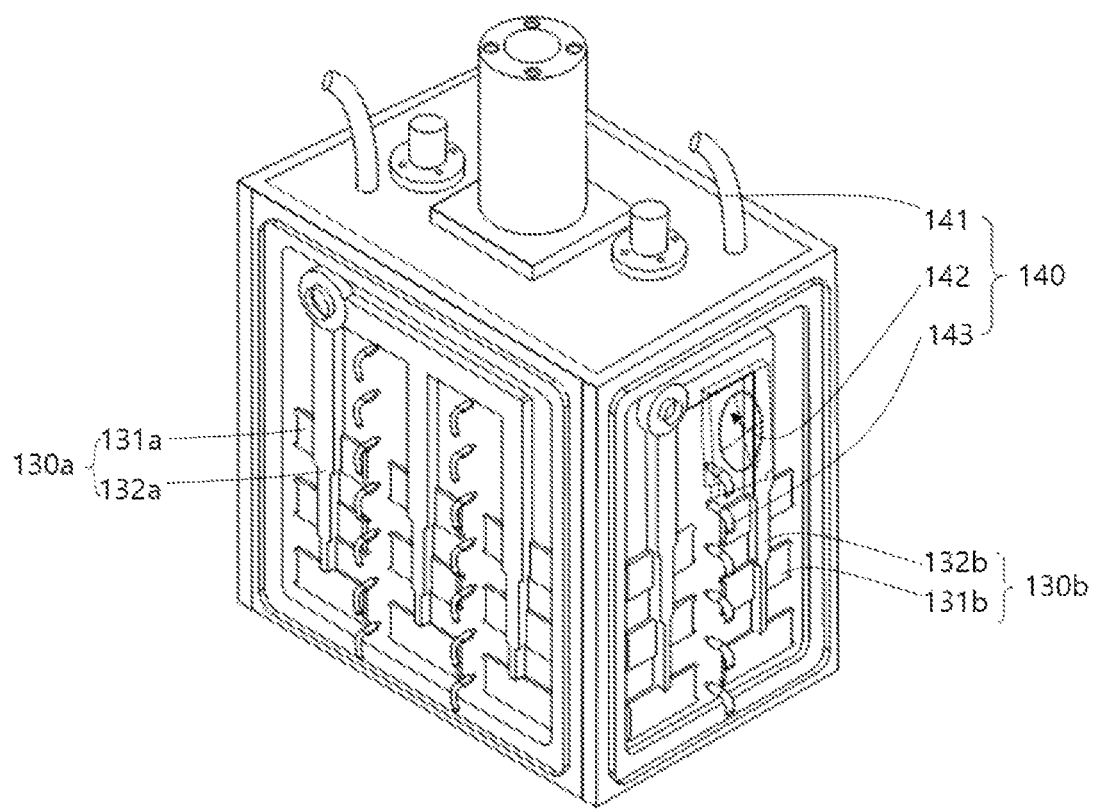

[FIG. 4]
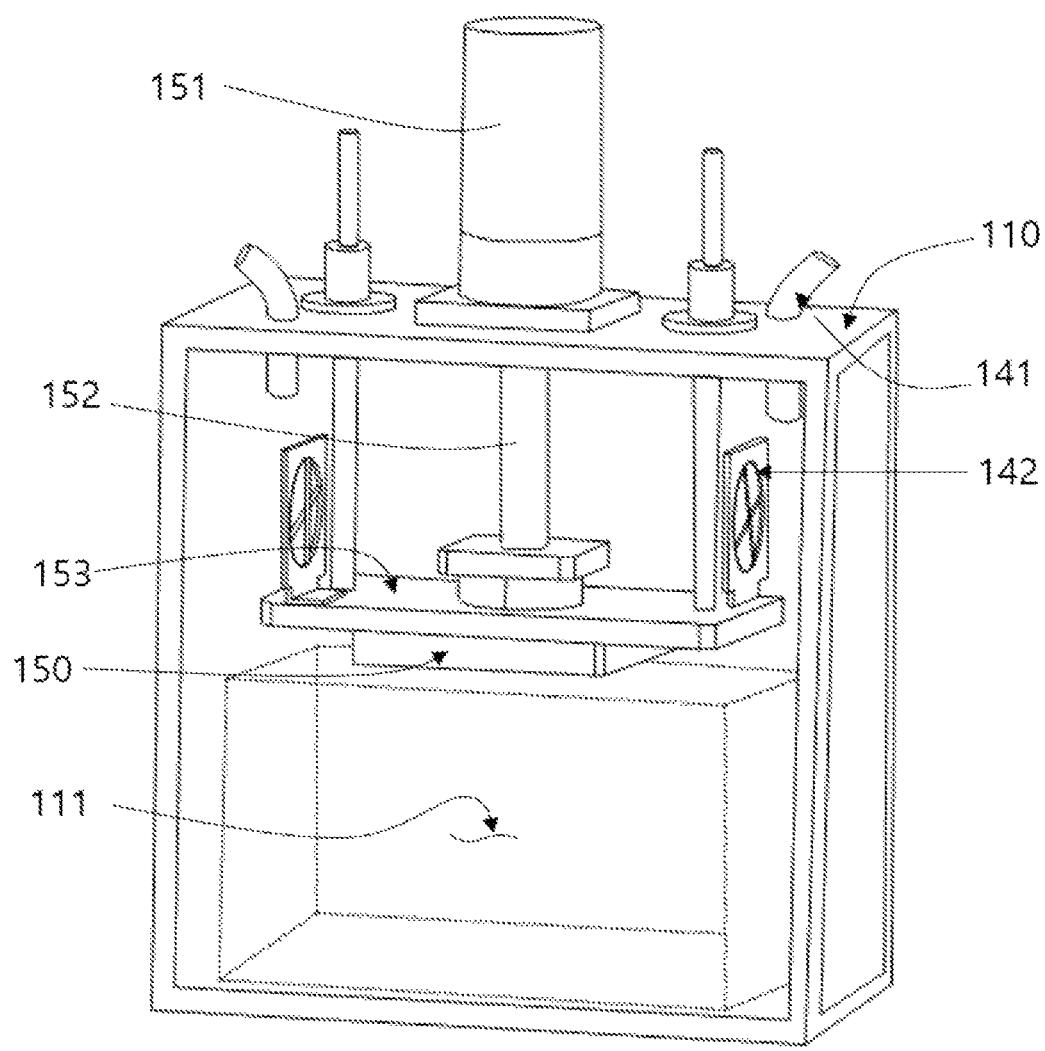

[FIG. 5]
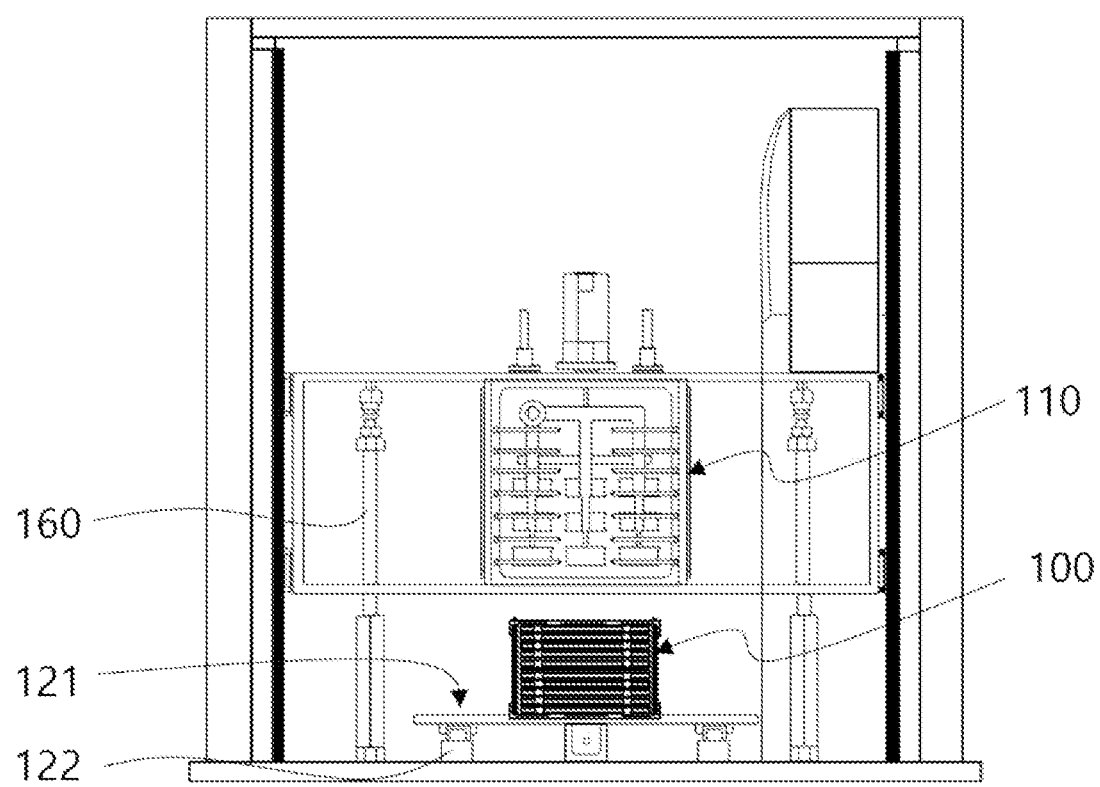

【FIG. 6】
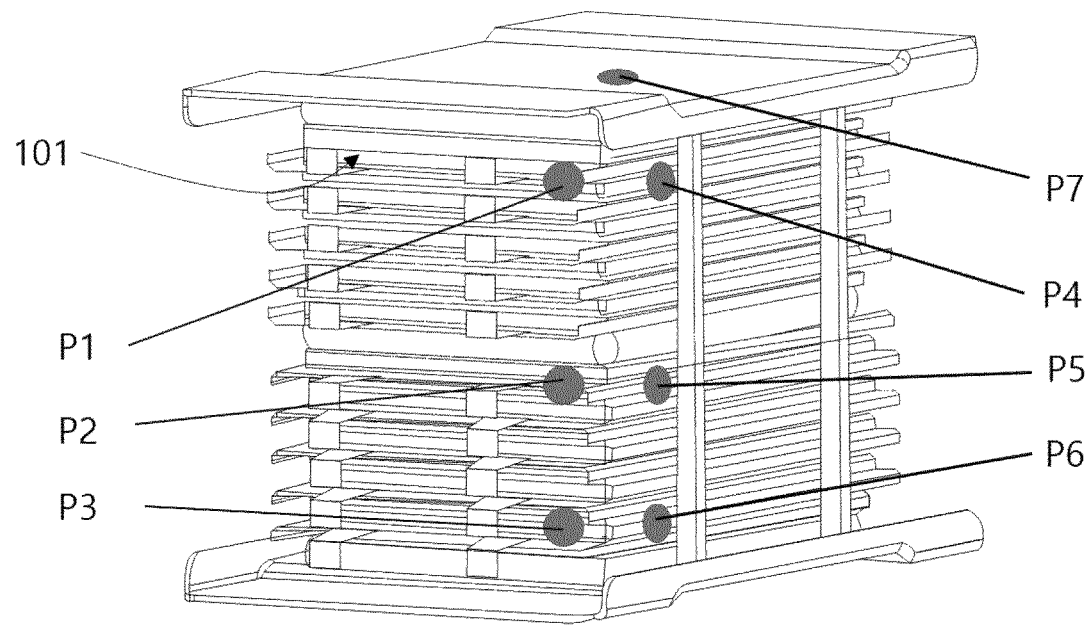
【FIG. 7】
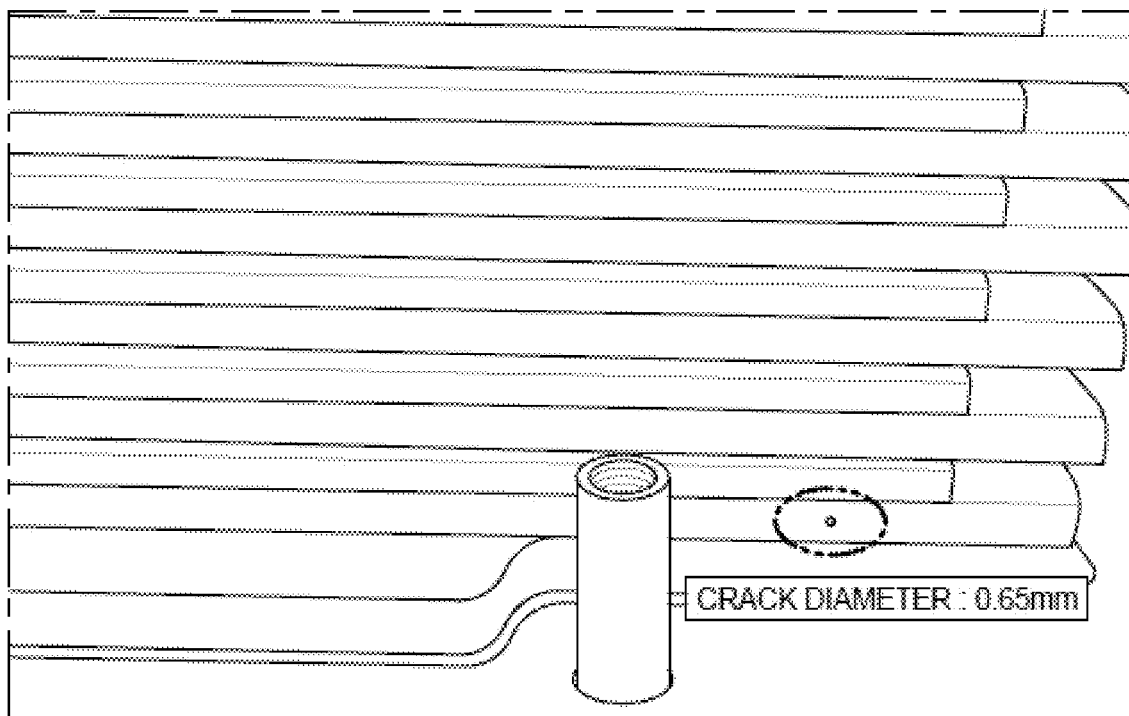

[FIG. 8]
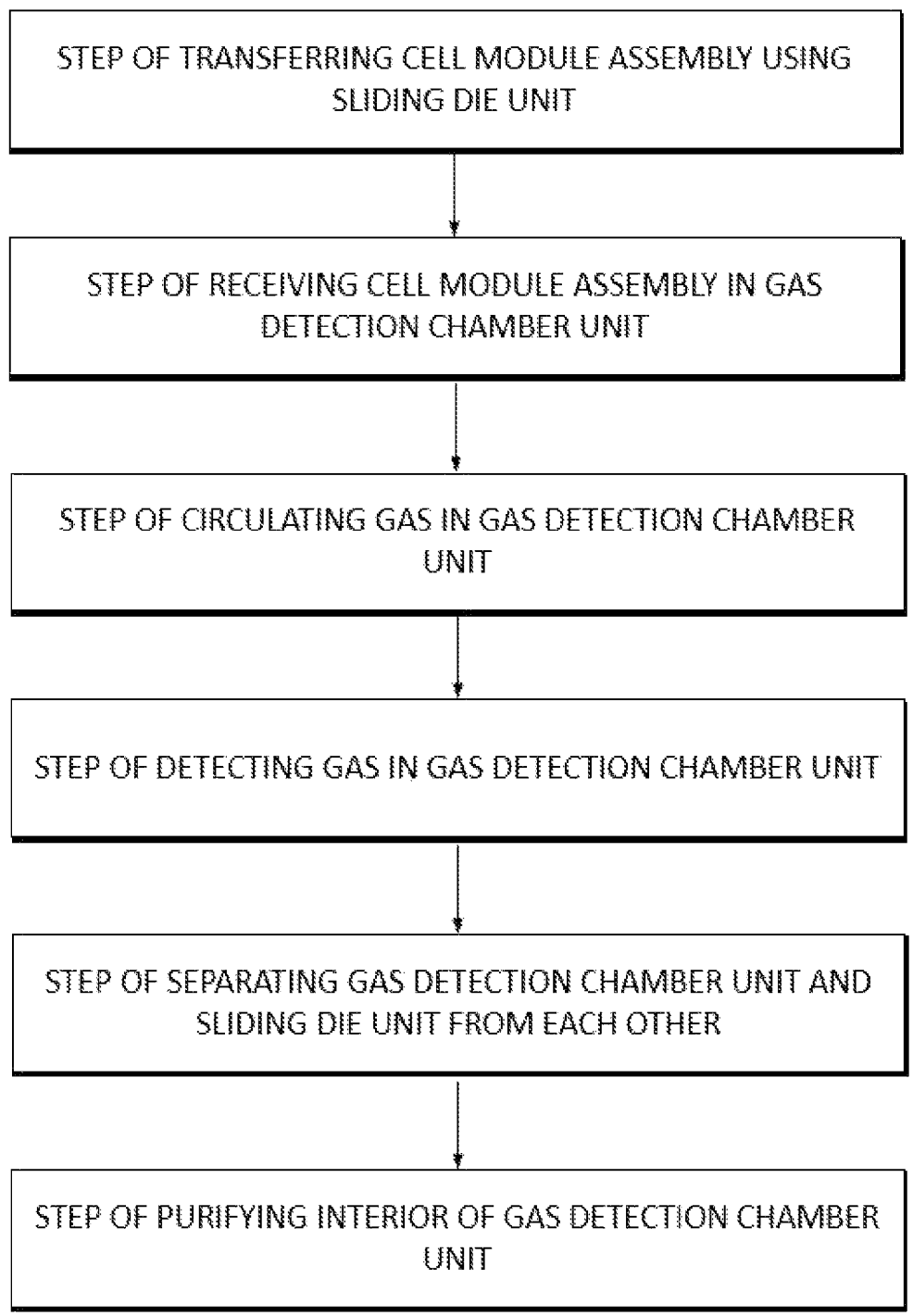

[FIG. 9]

| CLASSIFCATION | CRACK POSITION | ARRIVAL TIME (s) | DETECTED VALUE (ppm) |
|---|---|---|---|
| EXAMPLE 1 | P3 | 5 | 17,150 |
|  | P6 | 5 | 8,174 |
| EXAMPLE 2 | P3 | 3 | 11,250 |
|  | P6 | 2 | 13,531 |

[FIG. 10]

| CLASSIFCATION | CRACK POSITION | ARRIVAL TIME (s) | DETECTED VALUE (ppm) |
|---|---|---|---|
| EXAMPLE 3 | P1 | 4 | 11,232 |
|  | P4 | 4 | 6,993 |
| EXAMPLE 4 | P1 | 4 | 9,367 |
|  | P4 | 2 | 22,435 |

[FIG. 11]

| AIR CIRCULATION DEVICE | AIR FAN | | AIR BLOWER | | DETECTION RESULTS | | NUMBER OF DETECTED CHANNELS |
|---|---|---|---|---|---|---|---|
| DIVING TIME | 2s | CONTINUOUS | 2s | CONTINUOUS | ARRIVAL TIME(s) | MAX DETECTED VALUE (ppm) | |
| EXPERIMENTAL CONDITIONS | - | - | - | - | 3 | 57,330 | 32 |
| | O | - | - | - | 10 | 57,330 | 32 |
| | - | O | - | - | 3 | 31,821 | 26 |
| | - | - | O | - | 3 | 57,330 | 20 |
| | - | - | - | O | 4 | 32,418 | 11 |
| | O | - | O | - | 13 | 57,330 | 29 |
| | O | - | - | O | 4 | 40,563 | 21 |
| | - | O | O | - | 4 | 21,425 | 29 |
| | - | O | - | O | 4 | 32,239 | 9 |

[FIG. 12]

| CLASSIFICATION | AIR FAN | AIR SUCTION DEVICE | AIR BLOWER | CLEANING TIME (s) |
|---|---|---|---|---|
| EXPERIMENTAL CONDITIONS | - | - | - | 579 |
| | O | - | - | 13 |
| | - | O | - | 25 |
| | - | - | O | 35 |
| | O | O | - | 10 |
| | - | O | O | 11 |
| | O | - | O | 21 |
| | O | O | O | 9 |

[FIG. 13]

| CRACK POSITION | DETECTED |
|---|---|
| P1 | O |
| P2 | O |
| P3 | O |
| P4 | O |
| P5 | O |
| P6 | O |
| P7 | X |

[FIG. 14]
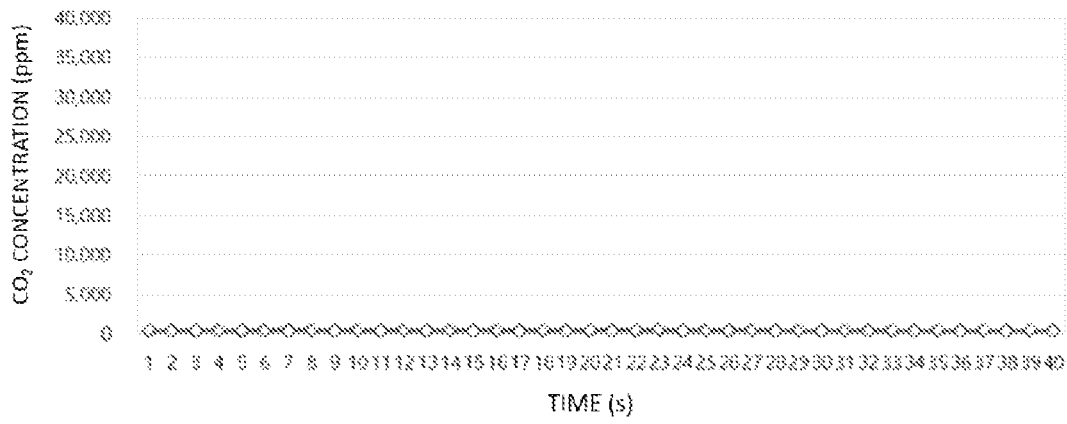
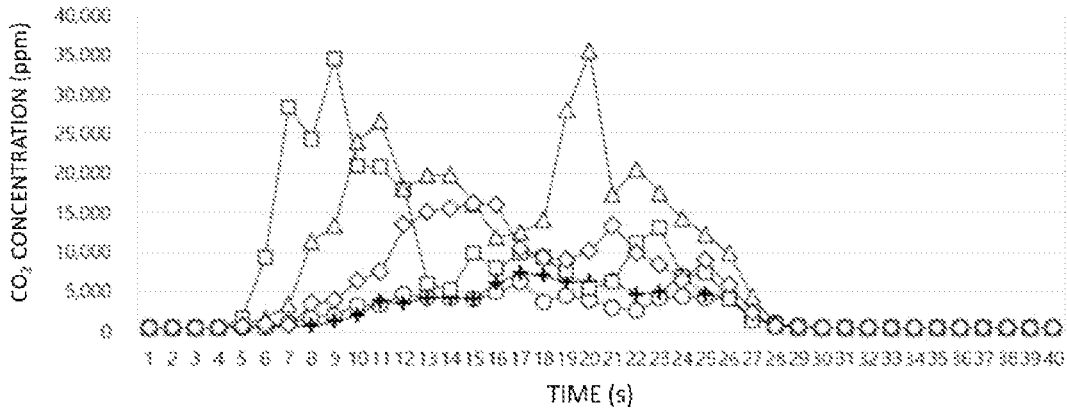

GAS DETECTION APPARATUS AND GAS DETECTION METHOD FOR CELL MODULE ASSEMBLIES

TECHNICAL FIELD

This application claims the benefit of priority to Korean Patent Application No. 2020-0094310 filed on Jul. 29, 2020, the disclosure of which is incorporated herein by reference in its entirety.

The present invention relates to a gas detection apparatus for cell module assemblies capable of accurately and rapidly detecting a cell having a damaged pouch of a battery cell module assembly and a damaged position of the cell and a gas detection method for cell module assemblies using the same.

BACKGROUND ART

Secondary batteries, which have high applicability and electrical properties, such as high energy density, have generally been used in electric vehicles (EV) or hybrid electric vehicles (HEV), each of which is driven using an electrical driving source, as well as portable devices. Such secondary batteries have attracted attention as a new energy source capable of increasing environmental friendliness and energy efficiency, since no by-products are generated as the result of use of energy in addition to a primary advantage in that it is possible to remarkably reduce the use of fossil fuels.

There are a lithium ion battery, a lithium polymer battery, a nickel-cadmium battery, a nickel-hydride battery, and a nickel-zinc battery as secondary batteries that are widely used at present. The operating voltage of a unit secondary battery cell, i.e. a unit battery cell, is about 2.5V to 4.2V. In the case in which output voltage higher than the above operating voltage is required, therefore, a plurality of battery cells may be connected to each other in series to constitute a battery pack. In addition, a plurality of battery cells may be connected to each other in parallel depending on required charge and discharge capacities of a battery pack in order to constitute the battery pack. Consequently, the number of battery cells included in the battery pack may be variously set depending on required output voltage or charge and discharge capacities.

Meanwhile, in the case in which a plurality of battery cells is connected to each other in series/parallel to constitute a battery pack, a battery module including a plurality of battery cells may be manufactured first, and a battery pack may be manufactured using a plurality of battery modules and other components, which is a general method.

Meanwhile, in the case in which a battery cell assembly is constituted by a plurality of battery cells in the battery module, each of the battery cells may be a pouch-shaped lithium polymer secondary battery cell.

In general, the lithium secondary battery is classified as a liquid electrolyte battery or a polymer electrolyte battery based on the kind of an electrolytic solution. A battery using a liquid electrolyte is called a lithium ion battery, and a battery using a polymer electrolyte is called a lithium polymer battery. In addition, various kinds of sheathing members may be used for the lithium secondary battery. Typically, a cylindrical sheathing member, a prismatic sheathing member, and a pouch sheathing member are used. An electrode assembly configured to have a structure in which a positive electrode plate, a negative electrode plate, and a separator interposed therebetween are stacked or wound is provided in the sheathing member of the lithium secondary battery.

Conventionally, in a device, such as a vehicle, to which a battery module including a plurality of stacked electrode assemblies is applied, an electrolytic solution leaks from a pouch cell constituting each electrode assembly due to damage to a pouch case thereof caused by external influence during a manufacturing/assembly process thereof, or toxic gases generated due to electrochemical reaction between an electrode, an active material, and an electrolytic solution is introduced into the vehicle.

In the case in which the electrolytic solution leaks from the pouch battery due to damage to or poor airtightness of the case, the product is determined to be defective. For this reason, leakage inspection is performed on a manufacturing process line. In general, inspection is performed using a method of checking a welded portion of a cap plate welded to the case using X-rays or with the naked eye.

However, X-ray inspection is less practicable since a process and equipment are complicated, and visual inspection has low reliability.

In order to solve the above problems, Korean Patent Application Publication No. 2018-0047359 discloses a method of capturing gas inside and outside a cell using a plurality of gas capturing tubes configured to capture gas to determine whether gas in the cell is discharged from the outside, and Korean Patent Application Publication No. 2012-0115835 discloses an apparatus that inspects a sealed state of a secondary battery using a vacuum chamber.

However, these methods, each of which inspects whether a pouch case is defective for a unit cell constituting a battery module, have a disadvantage in that it is difficult to accurately sort a battery cell having defects, such as tear or cracks, from battery cells modularized by stacking in a process of manufacturing a battery cell module assembly.

Therefore, there is a high necessity for technology capable of accurately and rapidly sorting battery cells having defective cases during a battery cell module assembly manufacturing process before delivery of final products.

Prior Art Documents (Patent Document 1) Korean Patent Application Publication No. 2018-0047359
(Patent Document 2) Korean Patent Application Publication No. 2012-0115835

DISCLOSURE

Technical Problem

The present invention has been made in view of the above problems, and it is an object of the present invention to provide a gas detection apparatus for cell module assemblies capable of accurately and rapidly detecting a cell having a damaged case of a battery cell module assembly and the damaged position of the cell having the damaged case. It is another object of the present invention to provide a gas detection method for cell module assemblies using the gas detection apparatus for cell module assemblies.

Technical Solution

In order to accomplish the above objects, the present invention provides a gas detection apparatus for cell module assemblies, the gas detection apparatus including a gas detection chamber configured to receive a cell module assembly having a plurality of cells; a sliding die configured to be movable to the lower part of the gas detection chamber when the cell module assembly is disposed at the upper surface of the sliding die, and a plurality of gas sensors disposed so at positions corresponding to positions of the plurality of cells of the cell module assembly.

The plurality of gas sensors may be provided at an outer wall of the gas detection chamber so as to be spaced apart from each other by a predetermined distance.

The gas detection apparatus may further include a press provided in the gas detection chamber, the press being configured to press an upper part of the cell module assembly.

The gas detection apparatus may further include a gas circulator provided in the gas detection chamber.

The gas circulator may include at least one selected from among an air suction device, an air fan, and an air blower.

The air suction device may include a duct extending through a wall of the gas detection chamber unit and a suction pump.

The air fan may be disposed at an upper end wall surface of the gas detection chamber and an upper end surface of the cell module assembly received in the gas detection chamber.

The air blower may extend through a side wall surface of the gas detection chamber at a predetermined position of the cell module assembly.

The gas detection chamber may be moved downwards so as to be physically coupled to the sliding die such that the gas detection chamber is partially sealed or completely sealed.

The gas detection chamber is coupled to a stripper via a coupling member so as to be reciprocated upwards and downwards.

The sliding die may include a mounting die and a sliding frame.

The present invention provides a gas detection method for cell module assemblies, the gas detection method including transferring a cell module assembly to the lower end of a gas detection chamber using a sliding die, moving the gas detection chamber downwards to receive the cell module assembly in the gas detection chamber, driving a gas circulator to circulate gas in the gas detection chamber, detecting the gas in the gas detection chamber using a gas sensor, moving the gas detection chamber upwards to open the gas detection chamber, and driving the circulator to purify the gas detection chamber unit, wherein a damaged cell of the cell module assembly and the damaged position of the damaged cell are detected by a plurality of gas sensors disposed in the gas sensor unit.

In moving the gas detection chamber, the upper part of the cell module assembly may be pressed using a press provided in the gas detection chamber.

In the present invention, additional constructions may be provided through possible combinations of the above constructions.

Advantageous Effects

According to the present invention, it is possible to accurately and rapidly detect a battery cell having a defective pouch, among battery cells constituting a cell module assembly, and the defective position of the battery cell.

In addition, according to the present invention, it is possible to sort and replace defective cells in a cell module assembly production process, whereby it is possible to reduce a cell module assembly defect rate.

DESCRIPTION OF DRAWINGS

FIG. 1 is a front view of a gas detection apparatus for cell module assemblies according to an embodiment of the present invention.

FIG. 2 is a perspective view of the gas detection apparatus for cell module assemblies according to the embodiment of the present invention.

FIG. 3 is a perspective view of a gas detection chamber unit of the gas detection apparatus for cell module assemblies according to the embodiment of the present invention.

FIG. 4 is a view showing the internal structure of the gas detection chamber unit according to the embodiment of the present invention.

FIG. 5 is a front view showing the state in which a cell module assembly according to an embodiment of the present invention is disposed at the lower end of the gas detection chamber unit.

FIG. 6 is a perspective view of a cell module assembly having cracks formed therein according to an embodiment of the present invention.

FIG. 7 is a photograph of a cell module assembly having a crack formed therein according to an embodiment of the present invention.

FIG. 8 is a flowchart of a gas detection method for cell module assemblies according to an embodiment of the present invention.

FIGS. 9 to 14 show results of gas detection experiments on the cell module assembly according to examples of the present invention.

BEST MODE

In the present application, it should be understood that the terms "comprises," "has," "disposes," "includes," etc. specify the presence of stated features, numbers, steps, operations, elements, components, or combinations thereof, but do not preclude the presence or addition of one or more other features, numbers, steps, operations, elements, components, or combinations thereof.

In addition, the same reference numbers will be used throughout the drawings to refer to parts that perform similar functions or operations. In the case in which one part is said to be connected to another part in the specification, not only may the one part be directly connected to the other part, but also, the one part may be indirectly connected to the other part via a further part. In addition, that a certain element is included does not mean that other elements are excluded, but means that such elements may be further included unless mentioned otherwise.

Hereinafter, the present invention will be described with reference to the accompanying drawings in order to assist in understanding the present invention.

FIG. 1 is a front view of a gas detection apparatus for cell module assemblies according to an embodiment of the present invention, and FIG. 2 is a perspective view of the gas detection apparatus for cell module assemblies according to the embodiment of the present invention.

Referring to FIGS. 1 and 2, the gas detection apparatus 10 for cell module assemblies includes a gas detection chamber unit 110, a sliding die unit 120, a gas sensor unit 130, a gas circulation unit 140, and a pressing unit 150. In addition, the sliding die unit 120 according to the embodiment of the present invention may include a mounting die 121 and a sliding frame 122, the gas sensor unit 130 may include a gas sensing portion 131 and a gas electrode portion 132, and the gas circulation unit 140 may include an air suction device 141, an air fan 142, and an air blower 143.

FIG. 3 is a perspective view of the gas detection chamber unit of the gas detection apparatus for cell module assemblies according to the embodiment of the present invention.

Referring to FIG. 3, the gas sensor unit 130 may be constituted by a plurality of gas sensors 130a and 130b provided at an outer wall of the gas detection chamber unit 110, and each of the plurality of gas sensors 130 may be a semiconductor type gas sensor. The gas sensing portion 131 is a portion that directly reacts with gas that leaks due to damage to a cell according to the present invention to indicate a change in resistance, and the gas electrode portion 132 is a portion that transmits an electrical signal from the gas sensing portion 131 to the outside. Each of the gas sensors 130 may be disposed at a corresponding one of cells constituting a cell module assembly 100, or may be disposed at a corresponding one of predetermined positions of the cells. The gas sensing portion 131 extends through the side wall of the gas detection chamber unit 110 such that one end of the gas sensing portion is disposed at the inner surface of the side wall of the gas detection chamber unit 110 so as to face an inner space of the gas detection chamber unit 110, and the other end of the gas sensing portion 131 is connected to the gas electrode portion 132. The gas sensing portion is connected to an external data logger (not shown), which realizes the kind and concentration value of a detected gas from the electrical signal from the gas sensing portion 131. The plurality of gas sensors 130 may be disposed respectively at the stacked cells of the cell module assembly 100 or at the predetermined positions of the cells so as to be spaced apart from each other by a predetermined distance, and the number of gas sensors is not particularly restricted. In addition, the plurality of gas sensors may be disposed respectively at outer surfaces of cases of the cells that face the outer wall of the gas detection chamber unit, or may be disposed respectively at the predetermined positions of the outer surfaces of the cases of the cells that face the outer wall of the gas detection chamber unit. Consequently, the gas sensors 130 are disposed at the cells included in the cell module assembly 100 or are disposed at the predetermined positions of the cells, whereby it is possible to check a cell having a damaged case, from among the cells of the cell module assembly, and/or the damaged position of the cell having the damaged case based on a detection result. In the cell module assembly production stage, therefore, it is possible to check a defect of a cell due to damage thereto in advance and to replace the damaged cell, whereby it is possible to reduce a cell module assembly defect rate.

The gas circulation unit 140 may include at least one selected from the group consisting of an air suction device 141, an air fan 142, and an air blower 143. However, the present invention is not limited thereto. The air suction device 141 may be constituted by a duct provided so as to extend through an upper wall surface of the gas detection chamber unit 110 and a suction pump (not shown) connected to the other end of the duct, and suctions air in the gas detection chamber unit 110 through driving of the suction pump. Preferably, one or more air suction devices 141 are provided. One or more air fans 142 may be provided in the gas detection chamber unit 110. Preferably, the air fan 142 may be disposed in a space defined between an inner upper end surface of the upper wall surface of the gas detection chamber unit 110 and an upper end surface of the cell module assembly received in the gas detection chamber unit 110, and one or more air fans 142 may be provided. The air blower 143 may be constituted by a nozzle (not shown) extending through the wall surface of the gas detection chamber unit 110 and an air hose (not shown) coupled to the nozzle. The air blower 143 may be disposed so as to extend through the upper wall surface or a side wall surface of the gas detection chamber unit 110. Preferably, the air blower is disposed spaced apart from the side wall surface of the gas detection chamber unit by a predetermined distance. One or more air blowers may be disposed depending on characteristics of the cell module assembly and other environments, and the number of air blowers is not particularly restricted.

FIG. 4 is a view showing the internal structure of the gas detection chamber unit according to the embodiment of the present invention.

Referring to FIG. 4, the air suction device 141 may be disposed so as to extend through the upper wall surface of the gas detection chamber unit 110, a central shaft 152 connected to a motor 151 disposed at an upper end wall of the gas detection chamber unit 110 may be disposed so as to extend through a central plate 153, and the pressing unit 150 may be coupled to an end of the central shaft 152 while being located at a lower end surface of the central plate 153. A receiving space 111 configured to receive the cell module assembly may be formed under the lower end of the pressing unit 150. In addition, the pressing unit 150 may press the upper end surface of the cell module assembly while pressing pressure thereof is adjusted using a method of controlling the lowering height of the pressing unit by driving of the motor 151.

FIG. 5 is a front view showing the state in which a cell module assembly according to an embodiment of the present invention is disposed at the lower end of the gas detection chamber unit.

Referring to FIG. 5, when the cell module assembly 100 disposed at the upper end of the mounting die 121 is located at the lower end of the gas detection chamber unit 110 along the sliding frame 122, the gas detection chamber unit 110 is moved downwards by downward operation of the stripper 160 mechanically coupled to the gas detection chamber unit 110, whereby the lower end surface of the side wall of the gas detection chamber unit 110 comes into tight contact with the upper surface of the mounting die 121 while the cell module assembly 100 is received in the receiving space in the gas detection chamber unit 110. Each of the gas detection chamber unit 110 and the mounting die 121 is provided with a fastening member (not shown), by which the inner space of the gas detection chamber unit 110 may be completely sealed. In addition, when gas detection is completed, the gas detection chamber unit 110 is moved upwards by upward operation of the stripper 160, whereby the cell module assembly 100 and the sliding die unit 120 are opened, and the sliding die unit 120 is moved to replace the cell module assembly with a cell module assembly to be inspected.

FIG. 6 is a perspective view of a cell module assembly having cracks formed therein according to an embodiment of the present invention.

Referring to FIG. 6, battery cells are stacked such that relatively wide surfaces of the battery cells face each other to constitute a cell module assembly, cracks p are formed in side surfaces of cases of the stacked battery cells 101 and in the upper surface of the uppermost battery cell that does not face the other battery cells or the lower part of the uppermost battery cell. The cracks may be distributed at various positions of the battery cells.

FIG. 7 is a photograph showing formation of a crack according to an embodiment of the present invention.

Referring to FIG. 7, a circular-hole-shaped crack is formed in the surface of the case of one of the stacked cells constituting the cell module assembly. The diameter of the crack is 0.65 mm.

FIG. 8 is a flowchart of a gas detection method for cell module assemblies according to an embodiment of the present invention.

Referring to FIG. 8, a method of detecting gas in a cell module assembly 100 using the gas detection apparatus for cell module assemblies includes a step of disposing the cell module assembly 100 at the upper end of the mounting die 121 of the sliding die unit 120 and transferring the cell module assembly 100 using the sliding die unit 120 such that the mounting die 121 is located at the lower end of the gas detection chamber unit 110 along the sliding frame 122; a step of moving the gas detection chamber unit 110 downwards through downward operation of the stripper 160 such that the lower surface of the gas detection chamber unit 110 comes into tight contact with the upper surface of the mounting die 121 in order to receive the cell module assembly 100 mounted at the upper part of the mounting die 121 in the gas detection chamber unit 110; a step of driving the gas circulation unit 140 to circulate gas in the gas detection chamber unit 110; a step of detecting the gas in the gas detection chamber unit 110 using the gas sensor unit 130; a step of moving the gas detection chamber unit 110 upwards through upward operation of the stripper 160 to separate the cell module assembly 100 and the sliding die unit 120 from the gas detection chamber unit; and a step of purifying the interior of the gas detection chamber unit 110 using the gas circulation unit 140.

Also, in the step of receiving the cell module assembly in the gas detection chamber unit 110, the lowering height of the stripper 160 may be adjusted, and the cell module assembly 100 may be pressed using the pressing unit 150.

FIGS. 9 to 14 show results of gas detection experiments on the cell module assembly according to examples of the present invention.

In the following examples of the present invention, the cell module assembly was disposed in the gas detection chamber unit 110 such that relatively long ones of the side surfaces of the stacked battery cells, excluding the stacked surfaces thereof, face the front wall surface and the rear wall surface of the gas detection chamber unit 110 and relatively short ones of the side surfaces of the stacked battery cells face the side wall surface of the gas detection chamber unit 110. In addition, a $CO_2$ detection sensor was used as the gas sensor.

Example 1

Cracks were formed at positions p3 and p6 of the cell module assembly 100 shown in FIG. 6, and gas detection experiments were performed.

The cell module assembly 100 having cracks formed at positions p3 and p6 was disposed on the mounting die 121, the mounting die 121 was moved along the sliding frame 122 so as to be located at the lower end of the gas detection chamber unit 110, the stripper 160 was driven downwards such that the lower surface of the gas detection chamber unit 110 came into close contact with the upper surface of the mounting die 121, gas in the gas detection chamber unit 110 was detected using the gas sensor unit 130 while the gas circulation unit 140 was driven to circulate the gas in the gas detection chamber unit 110, result values were transmitted to the external data logger, and detected $CO_2$ concentration values were collected.

Experiment times and $CO_2$ concentration detection values according to Example 1 are shown in FIG. 9.

Example 2

Gas detection experiments were performed in the state in which the interior of the gas detection chamber unit 110 was completely sealed.

Gas detection experiments were performed in the same manner as in Example 1 except that the lower surface of the gas detection chamber unit 110 and the upper surface of the mounting die 121 were fastened to each other via a fastening member such that the interior of the gas detection chamber unit was completely sealed.

Experiment times and $CO_2$ concentration detection values according to Example 2 are shown in FIG. 9.

Example 3

Gas detection experiments were performed in the state in which the cell module assembly 100 was not pressed in the gas detection chamber unit 110 that was partially sealed.

Cracks were formed at positions p1 and p4 of the cell module assembly 100 shown in FIG. 6, and gas detection experiments were performed.

The cell module assembly 100 having cracks formed at positions p1 and p4 was disposed on the mounting die 121, the mounting die 121 was moved along the sliding frame 122 so as to be located at the lower end of the gas detection chamber unit 110, the stripper 160 was driven downwards such that the lower surface of the gas detection chamber unit 110 came into close contact with the upper surface of the mounting die 121, gas in the gas detection chamber unit 110 was detected using the gas sensor unit 130 while the gas circulation unit 140 was driven to circulate the gas in the gas detection chamber unit 110, result values were transmitted to the external data logger, and detected $CO_2$ concentration values were collected.

Experiment times and $CO_2$ concentration detection values according to Example 3 are shown in FIG. 10.

Example 4

Gas detection experiments were performed in the state in which the cell module assembly 100 was pressed in the gas detection chamber unit 110 that was partially sealed.

Cracks were formed at positions p1 and p4 of the cell module assembly 100 shown in FIG. 6, and gas detection experiments were performed.

Gas detection experiments were performed in the same manner as in Example 3 except that a step of bringing the lower surface of the gas detection chamber unit 110 into close contact the upper surface of the mounting die 121 and further driving the stripper 160 downwards in the state in which the pressing unit 150 was disposed in contact with the upper end surface of the cell module assembly 100 in order to press the upper end surface of the cell module assembly 100 was added.

Experiment times and $CO_2$ concentration detection values according to Example 4 are shown in FIG. 10.

Example 5

Experiments on a gas circulation effect depending on change in operation conditions of the gas circulation unit 140 were performed in the state in which the interior of the gas detection chamber unit 110 was partially sealed and the cell module assembly 100 was not pressed.

The cell module assembly 100 having cracks formed therein was disposed on the mounting die 121, the mounting die 121 was moved along the sliding frame 122 so as to be located at the lower end of the gas detection chamber unit 110, the stripper 160 was driven downwards such that the lower surface of the gas detection chamber unit 110 came into close contact with the upper surface of the mounting die 121, gas in the gas detection chamber unit 110 was detected using the gas sensor unit 130, and result values were transmitted to the external data logger. In the step of detecting the gas using the gas sensor unit, the air fan 142 and the air blower 143 were individually or simultaneously driven either for 2 seconds or continuously to perform gas detection experiments.

Experiment times and $CO_2$ concentration detection values according to Example 5 are shown in FIG. 11.

Example 6

Experiments on an effect of purifying the gas detection chamber unit 110 depending on change in operation conditions of the gas circulation unit 140 were performed in the state in which the interior of the gas detection chamber unit 110 was partially sealed and the cell module assembly 100 was not pressed.

Gas detection experiments according to the present invention were performed using the cell module assembly 100 having cracks formed in the surfaces of the pouch cases of the cells, and experiments to purify the gas detection chamber unit 110 through driving of the gas circulation unit 140 were performed after gas detection.

It can be seen from the experiment results that the gas detection chamber unit was the most quickly purified when the air suction device 141, the air fan 142, and the air blower 143 were simultaneously driven.

Experiment times and $CO_2$ concentration detection values according to Example 6 are shown in FIG. 12.

Example 7

Gas detection experiments were performed in the same manner as in Example 1 except that gas detection was performed at positions p1, p2, p3, p4, p5, p6, and p7 of the cell module assembly 100 shown in FIG. 6.

It can be seen from the gas detection experiment result for each crack position according to Example 7 that the position of the crack formed in the upper surface of the uppermost cell of the cell module assembly was detected. For this reason, the surfaces of the stacked cells that face each other, i.e. the upper surface and the lower surface of each unit cell, form stacked surfaces, whereby an effect similar to a taping effect is achieved, and therefore gas detection due to gas leakage within a short time may be difficult. Consequently, it can be seen that it may be difficult to rapidly detect the positions of cracks formed in the stacked surfaces using the gas detection apparatus for cell module assemblies according to the present invention.

The results of $CO_2$ gas detection according to Example 7 are shown in FIG. 13.

Example 8

In Example 8, gas detection experiments were performed on a normal cell module assembly having no crack formed therein and a defective cell module assembly having a crack formed therein using the gas detection method according to the present invention. In this example, a defective cell module assembly having a crack formed at position P2 shown in FIG. 7 was used. Gas sensors were disposed at the front wall surface and the rear wall surface of the gas detection chamber unit 110 so as to be spaced apart from each other by a predetermined distance in a 3×3 matrix, and gas sensors were disposed at the side wall surface of the gas detection chamber unit so as to be spaced apart from each other by a predetermined distance in a 2×3 matrix. In addition, two gas sensors were also disposed at positions adjacent to the front of the upper wall surface of the gas detection chamber unit 110 so as to be spaced apart from each other by a predetermined distance. Experiments were performed through a step of transferring the cell module assembly using the sliding die unit 120; a step of moving the gas detection chamber unit 110 downwards through downward operation of the stripper 160 to receive the cell module assembly in the gas detection chamber unit 110; a step of driving the gas circulation unit 140 to circulate gas in the gas detection chamber unit 110; a step of detecting the gas in the gas detection chamber unit 110 using the gas sensor unit 130; a step of moving the gas detection chamber unit 110 upwards through upward operation of the stripper 160 to separate the gas detection chamber unit 110 and the sliding die unit 120 from each other; and a step of purifying the interior of the gas detection chamber unit 110 using the gas circulation unit 140.

The results of gas detection experiments according to Example 8 are shown in FIG. 14. In the result graph, the period from the start to 25 seconds of an x-axis, which indicates time, is a gas detection period, and the period from the 25 seconds to 40 seconds is a period during which the gas detection chamber unit 110 is purified after gas detection is completed. It can be seen from the result graph that gas was not detected as the result of gas detection experiments using the normal cell module assembly and that five gas sensors disposed at the crack position and the upper side, the lower side, the left side, and the right side of the crack position, among 34 gas sensors, detected $CO_2$ gas as the result of gas detection experiments using the cell module assembly having the cracks formed therein. The detected $CO_2$ concentration value was greater when the gas sensor was disposed closer to the crack position, and the average $CO_2$ concentration value of the gas sensor disposed closest to the crack position was the greatest. Consequently, it can be seen that it is possible to determine whether the battery cell is damaged based on whether $CO_2$ is detected by the gas sensor and that it is possible to determine a damaged cell and the damaged position of the cell based on comparison in $CO_2$ concentration values detected by the gas sensors.

Although the specific details of the present invention have been described in detail, those skilled in the art will appreciate that the detailed description thereof discloses only preferred embodiments of the present invention and thus does not limit the scope of the present invention. Accordingly, those skilled in the art will appreciate that various changes and modifications are possible, without departing from the category and technical idea of the present invention, and it will be obvious that such changes and modifications fall within the scope of the appended claims.

DESCRIPTION OF REFERENCE SYMBOLS

10: Gas detection apparatus for cell module assemblies
100: Cell module assembly
101: Cell 110: Gas detection chamber unit
111: Receiving space
120: Sliding die unit
121: Mounting die
122: Sliding frame
130, 130a, 130b: Gas sensor units
131, 131a, 131b: Gas sensing portions
132, 132a, 132b: Gas electrode portions
140: Gas circulation unit
141: Air suction device
142: Air fan
143: Air blower
150: Pressing unit
151: Motor
152: Central shaft
153: Central plate
160: Stripper
p, p1, p2, p3, p4, p5, p6, p7: Gas sensor detection positions detection positions

The invention claimed is:

1. A gas detection apparatus for cell module assemblies, the gas detection apparatus comprising:
a gas detection chamber configured to receive a cell module assembly having a plurality of cells;
a sliding die configured to be movable to a lower part of the gas detection chamber when the cell module assembly is disposed at an upper end of the sliding die;
a plurality of gas sensors disposed at positions corresponding to positions of the plurality of cells of the cell module assembly; and
a press provided in the gas detection chamber, the press being configured to press an upper part of the cell module assembly.

2. The gas detection apparatus according to claim 1, wherein the plurality of gas sensors is provided at an outer wall of the gas detection chamber so as to be spaced apart from each other by a predetermined distance.

3. The gas detection apparatus according to claim 1, further comprising a gas circulator provided in the gas detection chamber.

4. The gas detection apparatus according to claim 3, wherein the gas circulator comprises at least one selected from among an air suction device, an air fan, and an air blower.

5. The gas detection apparatus according to claim 4, wherein the air suction device comprises a duct extending through a wall of the gas detection chamber.

6. The gas detection apparatus according to claim 4, wherein the air fan is disposed at an upper end wall of the gas detection chamber.

7. The gas detection apparatus according to claim 4, wherein the air blower extends through a side wall surface of the gas detection chamber at a predetermined position of the cell module assembly.

8. The gas detection apparatus according to claim 1, wherein the gas detection chamber is moved downwards so as to be physically coupled to the sliding die such that the gas detection chamber is partially sealed or completely sealed.

9. The gas detection apparatus according to claim 1, wherein the gas detection chamber is coupled to a stripper so as to be reciprocated upwards and downwards.

10. The gas detection apparatus according to claim 1, wherein the sliding die comprises a mounting die and a sliding frame.

11. A gas detection method for cell module assemblies, the gas detection method comprising:
transferring a cell module assembly to a lower end of a gas detection chamber using a sliding die;
moving the gas detection chamber downwards to receive the cell module assembly in the gas detection chamber;
driving a gas circulator to circulate gas in the gas detection chamber;
detecting the gas in the gas detection chamber using a gas sensor;
moving the gas detection chamber upwards to open the gas detection chamber; and
driving the gas circulator to purify the gas detection chamber,
wherein, in moving the gas detection chamber, an upper part of the cell module assembly is pressed using a press provided in the gas detection chamber.

* * * * *